United States Patent [19]

Lo et al.

[11] Patent Number: 4,749,788

[45] Date of Patent: Jun. 7, 1988

[54] PROCESS FOR THE PREPARATION OF ARYL-PYRIDO(1,4) BENZODIAZEPINES

[75] Inventors: Young S. Lo; William J. Welstead, Jr., both of Richmond, Va.

[73] Assignee: A. H. Robins Company, Incorporated, Richmond, Va.

[21] Appl. No.: 37,794

[22] Filed: Apr. 13, 1987

[51] Int. Cl.⁴ .................................................. C07D 471/04
[52] U.S. Cl. ......................................... 540/557; 546/308; 540/495
[58] Field of Search ............................................. 540/557

[56] References Cited

U.S. PATENT DOCUMENTS

| | | | |
|---|---|---|---|
| 4,447,361 | 5/1984 | Taylor | 540/557 |
| 4,480,100 | 10/1984 | Lo et al. | 540/557 |
| 4,560,510 | 12/1985 | Lo et al. | 540/557 |

*Primary Examiner*—Robert T. Bond

[57] ABSTRACT

A process is described wherein pyrido[1,4]benzodiazepines having the formula:

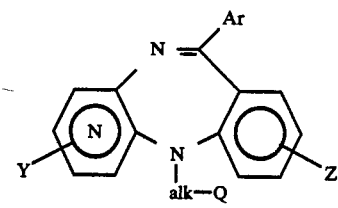

wherein Q is $NR^1R^2$ or

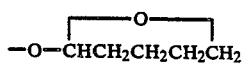

are prepared from unsubstituted pyridobenzodiazepinones by alkylation reaction with halo-alkyl-Q followed by acylation of the other nitrogen; breaking the ring with an aryl Grignard reagent and recyclizing to add the aryl radical and form the azepine ring. Novel intermediates are thereby disclosed.

1 Claim, No Drawings

PROCESS FOR THE PREPARATION OF ARYL-PYRIDO(1,4) BENZODIAZEPINES

BACKGROUND OF THE INVENTION

1. Field of Invention

The present invention relates to a new process for the preparation of certain known aryl-pyrido[1,4]benzodiazepines from pyridobenzodiazepinones and novel chemical intermediates involved therein.

2. Information Disclosure Statement

Certain of the aryl-pyrido[1,4]-benzodiazepines preparable by the process of the present invention and having aminoalkyl substitution on the solitary bridging nitrogen are disclosed in U.S. Pat. No. 4,447,361, the specification of which is hereby incorporated by reference to show in particular the formula numbering system used herein for compounds having varying pyridine nitrogen position. In the method of preparation disclosed in that patent, amino-halopyridine and aminoarylphenones were heated neat to give pyrido[1,4]benzodiazepines.

U.S. Pat. No. 4,560,510 discloses utilization of a strong non-nucleophilic base to bring about condensation of an aminochloropyridine and an aryl(aminophenyl)methanone in admixture with mobile inert carrier to produce pyrido[1,4]benzodiazepines. Preparation of pyrido[1,4]benzodiazepines of the present invention by that method having a

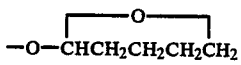

radical on the solitary bridging nitrogen atom and utility thereof in preparing the corresponding aminoalkyl-N-substituted compounds is disclosed therein.

U.S. Pat. No. 4,480,100 describes preparation of certain of the subject aryl-pyrido[1,4]benzodiazepines by cyclizing [2-[(aminopyridinyl)amino]phenyl]arylmethanones, the latter having been prepared from a nitro intermediate.

U.S. Pat. No. 4,558,132 describes preparation of aryl-pyrido[1,4]benzodiazepines by cyclizing aroylamino-N-phenylpyridineamines.

British Patent No. 1,456,627 and U.S. Pat. No. 4,021,557 disclose preparation of pyrido[2,3-b][1,4]benzodiazepinone having the formula:

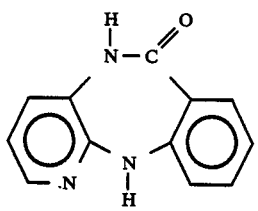

which is a precursor to starting compounds for the instant process. Aminoalkyl substitution on the solitary bridging nitrogen at the same time the other azepine nitrogen is substituted by a methyl group is also disclosed.

The procedure used in the instant process to acylate the unsubstituted nitrogen of N-substituted-pyridobenzodiazepinones in the initial step of the instant process and the subsequent reaction with Grignard reagent has similarity to that described by Gates, M. in J. ORG. CHEM. 45, 1675–1681 (1980) for synthesis of diazepam.

SUMMARY OF THE INVENTION

Pyridobenzodiazepine compounds prepared by the novel process of the invention and from the novel intermediates described herein have the formula:

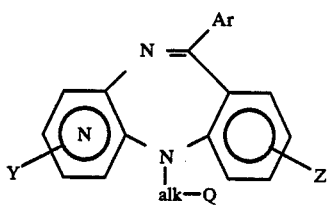

Formula I wherein;
Q is $-NR^1R^2$ or

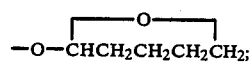

$R^1$ and $R^2$ are loweralkyl or $R^1$ and $R^2$ taken together with the adjacent nitrogen atom may form a heterocyclic residue selected from the group consisting of 1-pyrrolidinyl, 1-piperidinyl, 4-morpholinyl and 4-loweralkyl-piperazin-1-yl;

Ar is selected from phenyl, 2-fluorophenyl, 4-methylphenyl and 4-trifluoromethylphenyl;

Y and Z are selected from hydrogen, loweralkyl or loweralkoxy;

alk is a straight or branched connecting hydrocarbon chain of 1–8 carbons, and the acid addition salts thereof.

Certain novel N-[(benzoylphenyl)amino]pyridinyl]acetamide intermediates in the process have the formula:

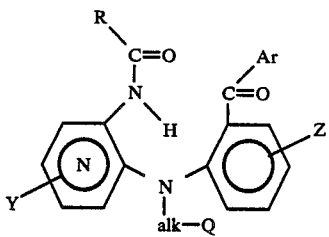

Formula II wherein Q, Y, Z, Ar and alk are as defined under Formula I and R is methyl or isopropyl.

Certain novel pyridobenzazepinone intermediates used in the process have the formula:

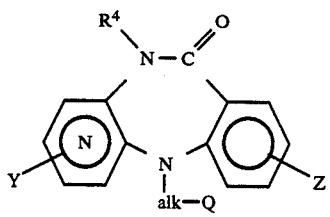

Formula III wherein;
Q, Y, Z and alk are as defined under Formula I above, and $R^4$ is hydrogen or

wherein R is methyl or isopropyl and the acid addition salts thereof.

In the further definition of symbols in the formulas herein and where they appear elsewhere throughout this specification and claims, the terms have the following significance.

The "alk" straight or branched connecting hydrocarbon chain containing 1-8 carbons is exemplified by methylene (—CH$_2$—), ethylene (—CH$_2$—CH$_2$—), propylene (—CH$_2$CH$_2$CH$_2$—), ethylidine [—CH—],
$\qquad\qquad\qquad\qquad\qquad\qquad\qquad$ |
$\qquad\qquad\qquad\qquad\qquad\qquad\qquad$ CH$_3$ 1,2-propylene [—CH—CH$_2$— or CH$_2$—C—],
$\qquad\qquad\qquad\quad$ |$\qquad\qquad\qquad\quad$ |
$\qquad\qquad\qquad\quad$ CH$_3$$\qquad\qquad\qquad\quad$ CH$_3$ $\qquad\qquad$ CH$_3$
$\qquad\qquad$ |
isopropylidine [—C—] or 1,3-butylene [—CH—CH$_2$—CH$_2$—
$\qquad\qquad$ |$\qquad\qquad\qquad\qquad\qquad\qquad\quad$ |
$\qquad\qquad$ CH$_3$$\qquad\qquad\qquad\qquad\qquad\qquad\quad$ CH$_3$ and the like.

The term "loweralkyl" includes straight and branched chain hydrocarbon radicals of up to eight carbon atoms inclusive and is exemplified by such groups as methyl, ethyl, isopropyl, butyl, isobutyl, tertiary butyl, amyl, isoamyl, hexyl, heptyl, octyl, and the like.

Acid addition salts are formed by either strong or weak acids. Representative of strong acids are hydrochloric, hydrobromic, sulfuric, and phosphoric acids. Representative of weak acids are fumaric, maleic, succinic, oxalic, cyclohexamic, and the like. Generally, when the end product of the process is one wherein Q is —NR$^1$R$^2$ and to be used as a pharmaceutical, as prepared, the acid used to prepare the salt would preferably be physiologically compatible in warm blooded animals. However, an acid addition salt may be converted to the free base compound regardless of the acid derivation by partitioning into an organic solvent in admixture with aqueous base solution and evaporating the solvent and, if desired, converting to any desirable acid salt. When Q is

any acid may be used to prepare the salt, inasmuch as the compound when utilized would then be converted to one in which Q is —NR$^1$R$^2$.

The process is outlined in brief by equation in Chart 1.

It is therefore a primary object of the invention to provide a novel route to aryl-pyrido[1,4]benzodiazepines having aminoalkyl substitution on the solitary bridging nitrogen.

Another object is to provide novel chemical intermediates useful in the preparation of aryl-pyrido[1,4]benzodiazepines of Formulas II and III.

Additional objects will be apparent to one skilled in the art and others will be apparent from the following description hereinbelow.

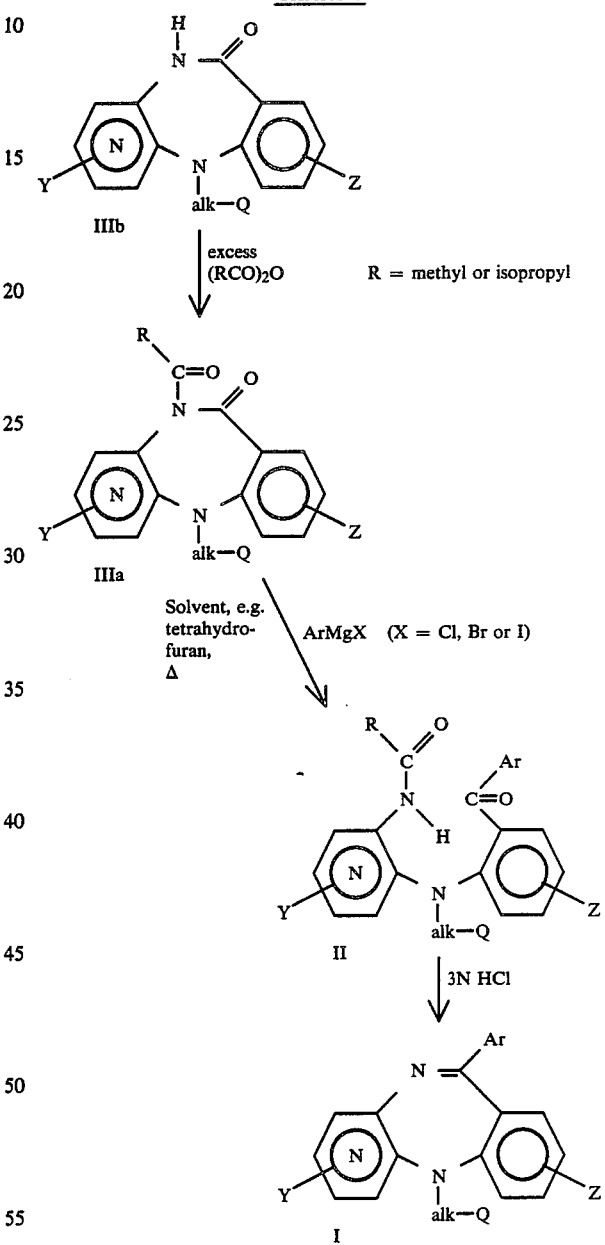

Footnote to Chart I:

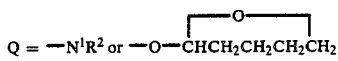

DETAILED DESCRIPTION OF THE INVENTION

The novel process for preparing the aryl-pyrido[1,4-]benzodiazepines of Formula I is comprised of the steps of:

Step 1, reacting a compound having the formula:

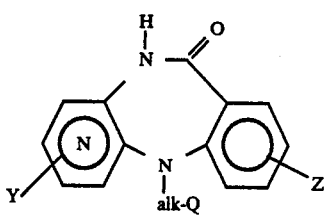

IIIb

wherein Y, Z, alk and Q are as defined under Formula I with an acid anhydride having the formula:

(RCO)₂O wherein R is methyl or isopropyl, to give a compound having the formula:

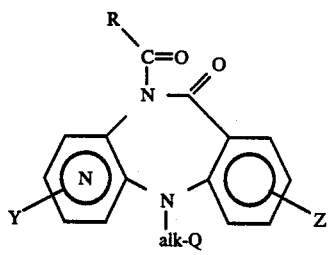

IIIa wherein Y, Z, R, alk and Q have their starting values;

Step 2, reacting a compound prepared in Step 1 with a Grignard reagent having the formula:

ArMgX wherein Ar is as defined under Formula I above and X is chloro, bromo or iodo, to give a mixture containing a compound selected from those having the formula:

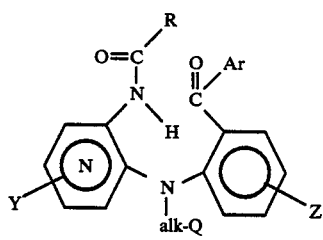

II wherein Ar, R, Y, Z, alk and Q are the same as in the starting reactants; and Step 3, heating the mixture obtained in Step 2 together with a strong acid to give a mixture containing an N-substituted-aryl-pyrido[1,4]benzodiazepine of Formula I and isolating said benzodiazepine from the mixture.

The preparation of starting Q-alk-substituted pyridobenzodiazepinones is illustrated in Charts 2 and 3.

Preparation 1 illustrates preparation of unsubstituted pyridobenzodiazepinones (V) (Chart 2) used to prepare pyridobenzodiazepinones in Example 1.

Preparations 2 and 3 illustrate preparation of N-(Q-alk)substituted benzamides (VIII) (Chart 3) used to prepare Q-alk-pyridobenzodiazepinones in Examples 2 and 3.

Examples 4-11 illustrate steps in the process outlined in Chart 1 and described above for converting Q-alk-pyridobenzodiazepinones IIIa and IIIb to give Q-alk-pyridobenzodiazepines of Formula I. Compounds of Formulas IIIa and IIIb are encompassed by Formula III above.

CHART 2

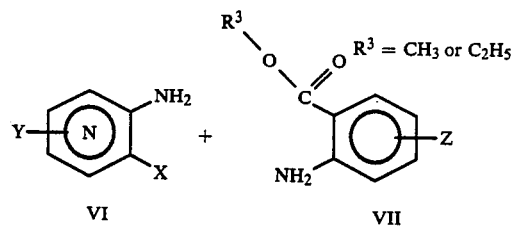

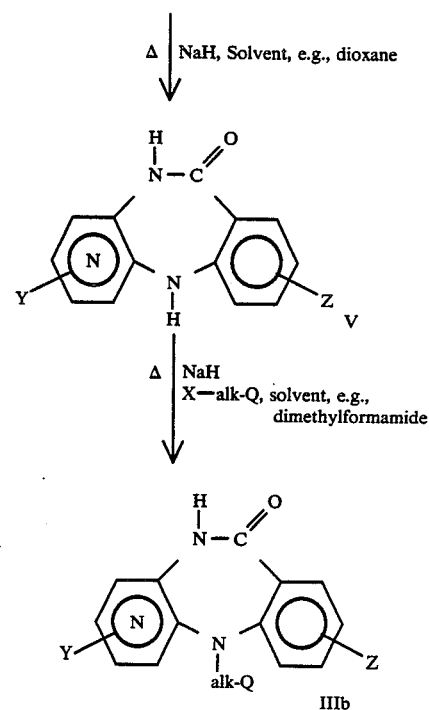

Footnote to Chart 2:

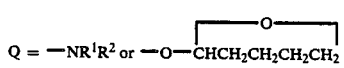

X = Cl, Br or I

CHART 3

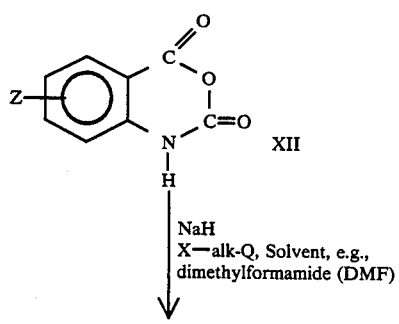

-continued
CHART 3

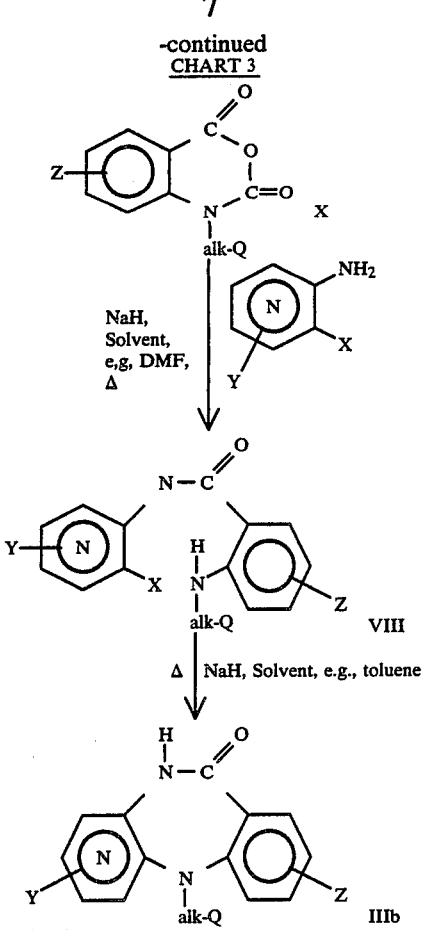

Footnote to Chart 3:

$Q = -NR^1R^2$ or $-O-\overset{\overset{\displaystyle O}{\displaystyle |\!\!-\!\!-\!\!-\!\!|}}{CHCH_2CH_2CH_2CH_2}$ $X = Cl, Br$ or $I$

PREPARATION 1

11H-Pyrido[2,3-b][1,4]benzodiazepin-6(5H)-one.
(Illustrates preparation of Formula V compounds of Chart 2).

To a mixture of 2 moles of sodium hydride in 650 ml of dioxane, cooled in an ice bath, was added 65 g (0.5 mole) of 3-amino-2-chloropyridine. To this mixture was added 65.3 ml (0.5 mole) of methyl anthranilate at rapid drop over a 7 min period. The mixture was then heated slowly to reflux and refluxed for about 3.5 hr. Heating was stopped and the mixture was cooled using an ice bath. A solution of 2.0 moles of ammonium chloride in 600 ml of water was added followed by 300 ml more water. The suspension was stirred for ½ hr and filtered. The solid was rinsed 4 times with water until neutral and then rinsed 2 times with isopropyl alcohol and 2 times with isopropyl ether, air dried, screened and dried under vacuum to give 74.11 g (70%) of solid. Proton NMR analysis showed the product was the title compound and a small amount of water and a small amount of 2-amino[N-(2-methoxypyridin-3-yl)]benzamide.

Preparation 2

N-(2-Chloro-3-pyridinyl)-2-[[3-(dimethylamino)propyl]amino]benzamide. (Illustrates Preparation of Formula VIII Compounds of Chart 3).

To a suspension of 9.6 g (0.24 mole) of 60% sodium hydride in 120 ml of dimethylformamide was added with cooling, 34 g (0.2 mole) of isatoic anhydride. The reaction mixture was heated at 50° C. for one hour and a solution of 3-dimethylaminopropyl chloride prepared as in Example 1 below from 49.4 g (0.3 mole) of the hydrochloride salt was added. The mixture was stirred overnight without heating. A sample was taken out and quenched with methanol. Mass spectroscopy analysis showed alkylation was incomplete. The reaction mixture was heated to reflux for 2 hr. This time mass spectroscopy analysis showed alkylation was complete. The reaction mixture was cooled in a water bath during which time 26 g (0.2 mole) of 3-amino-2-chloropyridine and 0.5 mole of sodium hydride were added. The temperature of the reaction mixture was carefully raised to reflux temperature (120° C.) over a 3 hr period and held at reflux for one hour. The reaction mixture was cooled and about 0.5 mole of ammonium chloride dissolved in water, 100 ml water, 50 ml toluene and 50 ml ethyl acetate were added. The organic layer was separated and washed once with water. Utilizing the following acid-base transfer extraction method the organic layer was extracted twice with dilute acetic acid and the aqueous layers were back extracted with toluene-ethyl acetate once and made basic with 50% aqueous sodium hydroxide solution in the presence of toluene-ethyl acetate mixture. The basic aqueous layer was extracted again with toluene-ethyl acetate. The toluene-ethyl acetate layers were back extracted with water. The organic layer was dried over sodium sulfate and concentrated to give 37.2 g of dark-brown oil. Proton NMR showed this oil to be mainly N-(2-chloro-3-pyridinyl)-2-[[3-(dimethylamino)propyl]amino]benzamide. (See Chart 3, Formula VIII).

Preparation 3

(Further illustrates preparation of Formula VIII compounds of Chart 3).

Following the procedure of the first part of Preparation 2, starting with isatoic anhydride and substituting the following for 2-amino-2-chloropyridine:
 4-amino-3-chloropyridine,
 3-amino-4-chloropyridine, and
 2-amino-3-chloropyridine, there are obtained as intermediates:
 N-(3-chloro-4-pyridinyl)-2-[[3-(dimethylamino)propyl]amino]benzamide hydrochloride,
 N-(4-chloro-3-pyridinyl)-2-[[3-(dimethylamino)propyl]amino]benzamide hydrochloride,
 N-(3-chloro-2-pyridinyl)-2-[[3-(dimethylamino)propyl]amino]benzamide hydrochloride.

Preparation 4

(Further illustrates preparation of Formula VIII compounds of Chart 3).

Following the procedure of the first part of Preparation 2, starting with isatoic anhydride and substituting 1-chloro-3-(tetrahydro-2H-pyran-2-yloxy) propane for 3-dimethylaminopropyl chloride and adding each of the following:
 2-amino-2-chloropyridine,
 4-amino-3-chloropyridine,
 3-amino-4-chloropyridine, and
 2-amino-3-chloropyridine, there are obtained as intermediates:
 (a) N-(2-chloro-3-pyridinyl)-2-[[3-(tetrahydro-2H-pyran-2-yloxy)propyl]amino]benzamide, (b) N-(3-chloro-4-pyridinyl)-2-[[3-(tetrahydro-2H-pyran-2-yloxy)propyl]amino]benzamide,
(c) N-(4-chloro-3-pyridinyl)-2-[[3-(tetrahydro-2H-pyran-2-yloxy)propyl]amino]benzamide,
(d) N-(3-chloro-2-pyridinyl)-2-[[3-(tetrahydro-2H-pyran-2-yloxy)propyl]amino]benzamide.

EXAMPLE 1

11-[3-(Dimethylamino)propyl]-11H-pyrido[2,3-b][1,4]benzodiazepin-6(5H)-one hydrochooride.

(Illustrates preparation of Formula IIIb compounds. Chart 2).

Preparation of solution of 3-dimethylaminopropyl chloride solution.

To a mixture of 24.7 g (0.15 mole) of 3-dimethylaminopropyl chloride hydrochloride and 40 ml of toluene was added with stirring, 13.0 g (0.16 mole) of 50% sodium hydroxide. The toluene solution was then decanted from the paste. The paste was triturated three times with 20 ml each of toluene, decanting the toluene each time. All of the toluene solutions were combined and dried over molecular seives 3A for 2 hr prior to use in this example and other following examples.

Aminoalkylation of the Benzodiazepinone.

A 12 g (0.3 mole) sample of 60% sodium hydride was added to dimethylformamide (DMF) with stirring and cooling. 11H-Pyrido[2,3-b][1,4]benzodiazepin-6(5H)-one, 21.1 g (0.10 mole) as a powder, was added and rinsed in with dimethylformamide (DMF). The total DMF used was 100 ml. The reaction mixture was warmed to 55° C. for 10 min, then cooled down to 35° C. and the 3-dimethylaminopropyl chloride solution, as prepared above, was added. The reaction mixture was slowly heated to 65° C. over a one hour period, after which it was allowed to cool to room temperature overnight. The reaction mixture was treated with saturated ammonium chloride solution and diluted with toluene. Precipitate, 2.6 g, was filtered off and identified as starting 11H-pyrido[2,3-b][1,4]benzodiazepin-6(5H)-one. The filtrate separated into two layers, an aqueous layer and a toluene layer. The aqueous layer was extracted four times with toluene. All toluene layers were back washed with water, dried over sodium sulfate and concentrated to give a dark brown oil. The oil was suspended in a mixture of isopropanol and isopropyl ether. The mixture was filtered to remove a small amount of starting 11H-pyrido[2,3-b][1,4]benzodiazepin-6(5H)-one. The filtrate was acidified with a solution of hydrogen chloride in isopropanol. The solid was collected by filtration and rinsed with isopropyl ether and dried to give 27.6 g of product in 83% yield, m.p. 174°–178° C. Mass spectroscopy showed (M+1)+: m/e 297. Proton NMR analysis of a sample dissolved in D$_2$O and basified with KOD and extracted with DCCL$_3$ (ppm) was found to be as follows: 8.20 to 6.80 (multiplet, 7H, aromatic): 3.95 (triplet, 2H, methylene protons of the propylene chain next to the ring nitrogen): 2.20 (singlet, 6H, methyl protons of the dimethylamino group); 2.55 to 1.55 (multiplet, 4H, methylene protons of the remainder of the propylene chain); 1.20 (multiplet, methyl protons of the residual 2-propanol and isopropyl ether).

EXAMPLE 2

11-[3-(Dimethylamino)propyl]-1H-pyrido[2,3-b][1,4]benzodiazepine-6(5H)-one hydrochloride.

(Illustrates preparation of Formula IIIb compounds from benzamides of Chart 3).

The oil obtained in Preparation 2, 37.2 g, identified as mainly N-(2-chloro-3-pyridinyl)-2-[[3-(dimethylamino)propyl]amino]benzamide, was dissolved in 250 ml of toluene and the solution was heated to distill out about 25 ml of solvent. To the solution which was cooled in an ice bath, under nitrogen atmosphere, was added 0.3 mole of 60% sodium hydride. The mixture was heated at reflux for 3.5 hr. The reaction mixture was cooled and ammonium chloride solution was added to consume the excess sodium hydride. The product was isolated by an acid-base transfer extraction method as described in Preparation 2 (after the sodium hydride addition described therein). An oil, 30.8 g, was obtained and dissolved in isopropyl alcohol. The solution was acidified with a solution of hydrogen chloride in isopropyl alcohol. The dried solid, 34.4 g, (52% yield based on starting isatoic anhydride in Preparation 2) was shown by comparative analysis with the product of Example 1, by TLC, proton and carbon 13 NMR analysis and by mass spectroscopy to be the title compound, the same as the compound of Example 1.

EXAMPLE 3 (a to g)

Further illustrates preparation of Formula IIIb compounds from benzamides).

Following the procedure of Example 2 and substituting the following free bases of the benzamides preparable in Preparations 3 and 4 for N-(2-chloro-3-pyridinyl)-2-[[3-(dimethylamino)propyl]amino]benzamide:

N-(3-chloro-4-pyridinyl)-2-[[3-(dimethylamino)propyl]amino]benzamide,
N-(4-chloro-3-pyridinyl)-2-[[3-(dimethylamino)propyl]amino]benzamide,
N-(3-chloro-2-pyridinyl)-2-[[3-(dimethylamino)propyl]amino]benzamide,
N-(2-chloro-3-pyridinyl)-2-[[3-(tetrahydro-2H-pyran-2-yloxy)propyl]amino]benzamide,
N-(3-chloro-4-pyridinyl)-2-[[3-(tetrahydro-2H-pyran-2-yloxy)propyl]amino]benzamide,
N-(4-chloro-3-pyridinyl)-2-[[3-(tetrahydro-2H-pyran-2-yloxy)propyl]amino]benzamide, and
N-(3-chloro-2-pyridinyl)-2-[[3-(tetrahydro-2H-pyran-2-yloxy)propyl]amino]benzamide, there are obtained:

(a) 11-[3-(dimethylamino)propyl]-11H-pyrido[3,4-b][1,4]benzodiazepin-6(5H)-one hydrochloride,
(b) 5-[3-(dimethylamino)propyl]-5H-pyrido[4,3-b][1,4]benzodiazepin-10(11H)-one hydrochloride,
(c) 5-[3-(dimethylamino)propyl]-5H-pyrido[3,2-b][1,4]benzodiazepin-10(11H)-one hydrochloride,
(d) 11-[3-(tetrahydro-2H-pyran-2-yloxy)propyl]-11H-pyrido[2,3-b][1,4]benzodiazepin-6(5H)-one hydrochloride,
(e) 11-[3-(tetrahydro-2H-pyran-2-yloxy)propyl]-11H-pyrido[3,4-b][1,4]benzodiazepin-6(5H)-one hydrochloride,
(f) 5-[3-(tetrahydro-2H)-pyran-2-yloxy)propyl]-5H-pyrido[4,3-b][1,4]benzodiazepin-10(11H)-one hydrochloride, and (g) 5-[3-(tetrahydro-2H-pyran-2-yloxy)propyl]-5H-pyrido[3,2-b][1,4]benzodiazepin-10(11H)-one hydrochloride.

EXAMPLE 4

11-[3-(Dimethylamino)propyl]-5-[2-methyl-1-oxopropyl]-11H-pyrido[2,3-b][1,4]benzodiazepin-6(5H)-one.

(Illustrates preparation of Formula IIIa compounds of Chart 1).

11-[3-(Dimethylamino)propyl]-11H-pyrido-[2,3-b][1,4]benzodiazepin-6(5H)-one, 12.8 g (0.043 mole)(free base obtained as brown oil by partitioning the hydrochloride salt between aqueous sodium hydroxide solution and toluene and evaporating the toluene layer) was mixed with 60 ml of isobutyric acid anhydride. The mixture was stirred in an oil both at 150°–174° C. for 4.5 hr. The mixture was cooled and diluted with 1:1 mixture of toluene-ethylacetate and extracted twice with 2N hydrochloric acid. The aqueous layers were separately back extracted with toluene-ethylacetate and then combined. The acidic combination (solution) was then added to a chilled mixture of methylene chloride, sodium bicarbonate and water with stirring to give a slightly basic mixture. The layers were separated and the aqueous layer was extracted once with methylene chloride. The organic layers were combined and back washed with water, dried over sodium sulfate, filtered and concentrated to give 9.86 g (68%) of brown oil which was the title compound and some solvent. Mass spectroscopy showed (m+1) m/e 367. Proton NMR analysis ($CDCl_3$, ppm) was found as follows: 8.3 to 6.90 (multiplet, 7H aromatic); 5.25 (singlet, residual methylene chloride); 4.5 to 3.20 (multiplet, 3H, methine proton of the 2-methyl-1-oxopropyl group and the methylene protons in the propylene chain next to the solitary bridging nitrogen); 2.20 (singlet, 6H, protons on the dimethylamino group); 2.45 to 1.60 (multiplet, 4H, methylene for protons on the remainder of the propylene chain); 1.50 to 0.95 (broad multiplet, 6H, methyl protons on the 2-methyloxopropyl group).

EXAMPLE 5

5-Acetyl-11-[3-(dimethylamino)propyl]-11H-pyrido[2,3-b][1,4]benzodiazepin-6(5H)-one.

(Illustrates preparation of Formula IIIa compounds of Chart 1).

Utilizing the general procedure of Example 4 and substituting an equal molar amount of acetic acid anhydride, the title compound was prepared via the intermediate N-[2-[(2-benzoylphenyl)(3-(dimethylamino)propyl]amino]-3-pyridinyl]acetamide in 61% yield as a brown oil having the following characteristics: Mass spectroscopy showed (M+1)+ =m/e 339; Proton NMR analysis ($CDCl_3$, ppm) was found to be as follows: 8.35 to 6.90 (multiplet, 7H, aromatic and residual toluene); 4.50 to 3.60 (broad, 2H, methylene protons next to the ring nitrogen; 2.60 (singlet, 3H, methyl protons of the acetyl group); 2.35 (singlet, methyl protons of the residual toluene); 2.20 (singlet, 6H, methyl protons of the dimethylamino group; 2.50 to 2.60 (multiplet, 4H, methylene protons on the remainder of propylene chain).

EXAMPLE 6 (a to c)

(Illustrates preparation of Formula IIIa compounds of Chart 1).

Following the procedure of Example 4, but substituting acetic acid anhydride for isobutyric acid anhydride and substituting the following for 11-[3-(dimethylamino)propyl]-11H-pyrido[2,3-b][1,4]benzodiazepin-6(5H)-one:

11-[3-(dimethylemino)propyl]-11H-pyrido[3,4-b][1,4]benzodiazepin-6(5H)-one,

5-[3-(dimethylamino)propyl]-5H-pyrido[4,3-b][1,4]benzodiazepin-10(11H)-one, and

5-[3-(dimethylamino)propyl]-5H-pyrido[3,2-b][1,4]benzodiazepin-10(11H)-one, there are obtained:

(a) 5-acetyl-11-[3-(dimethylamino)propyl]-11H-pyrido[3,4-b][1,4]benzodiazepin-6(5H)-one, (b) 11-acetyl-5-[3-(dimethylamino)propyl]-5H-pyrido[4,3-b][1,4]benzodiazepin-10(11H)-one, and (c) 11-acetyl-5-[3-(dimethylamino)propyl]-5H-pyrido[3,2-b][1,4]benzodiazepin-10(11H)-one.

EXAMPLE 7 (a to d)

(Illustrates preparation of Formula IIIb compounds of Chart 1).

Following the procedure of Example 4 and substituting acetic acid anhydride for isobutyric acid anhydride and the following for 11-[3-(dimethylamino)propyl]-11H-pyrido[2,3-b][1,4]benzodiazepin-6(5H)-one:

11-[3-(tetrahydro-2H-pyran-2-yloxy)propyl]-11H-pyrido[2,3-b][1,4]benzodiazepin-6(5H)-one, 11-[3-(tetrahydro-2H-pyran-2-yloxy)propyl]-11H-pyrido[3,4-b][1,4]benzodiazepin-6(5H)-one, 5-[3-(tetrahydro-2H-pyran-2-yloxy)propyl]-5H-pyrido[4,3-b][1,4]benzodiazepin-10(11H)-one, 5-[3-(tetrahydro-2H-pyran-2-yloxy)propyl]-5H-pyrido[3,2-b][1,4]benzodiazepin-10(11H)-one, and there are obtained:

(a) 5-acetyl-11-[3-(tetrahydro-2H-pyran-2-yloxy)-propyl]-11H-pyrido[2,3-b][1,4]benzodiazepin-6(5H)-one, (b) 4-acetyl-11-[3-(tetrahydro-2H-pyran-2-yloxy)propyl]-11H-pyrido[3,4-b][1,4]benzodiazepin-6(5H)-one, (c) 11-acetyl-5-[3-(tetrahydro-2H-pyran-2-yloxy)-propyl]-5H-pyrido[4,3-b][1,4]benzodiazepin-10(11H)-one, and (d) 11-acetyl-5-[3-(tetrahydro-2H-pyran-2-yloxy)-propyl]-5H-pyrido[3,2-b][1,4]benzodiazepin-10(11H)-one.

EXAMPLE 8

(Illustrates preparation of Formula II compounds of Chart 1).

Mixture containing N-[2-[(2-benzoylphenyl)-[3-(dimethylamino)]propyl]amino-3-pyridinyl]isobutyramide.

To a solution of 9.26 g (0.256 mole) of 11-[3-(dimethylamino)propyl]-5-[2-methyl-1-oxopropyl]-11H-pyrido[2,3-b][1,4]benzodiazepin-6(5H)-one, as prepared in Example 4, in 40 ml of tetrahydrofuran (THF) while stirring in an ice bath was added 16.7 ml of a 2.3 molar THF solution containing 0.384 mole of phenyl magnesium chloride over a 2 minute period. The ice bath was removed. Four hours later another 10 ml of the above Grignard solution was added and 3 hr later another 10 ml portion was added. Total additional phenyl magnesium chloride added was 0.46 mole. After stirring at room temperature overnight the reaction mixture was heated at reflux for 2 hr. The mixture was cooled in an ice bath and the excess Grignard reagent was consumed by adding ammonium chloride solution. The compounds were isolated by acid-base transfer extraction described in Preparation 2, drying and concentrating. Reddish brown oil, 5.23 g, was obtained. Proton NMR showed the oil to be a 1:2:1 molar mix of the following:

N-[2-[(2-benzoylphenyl)[3-(dimethylamino)propyl]amino-3-pyridinyl]isobutyramide, Starting 11-[3-(dimethylamino)propyl]-5-[2-methyl-1-oxopropyl]-11H-pyrido[2,3-b][1,4]benzodiazepin-6(5H)-one, and 11-[3-(dimethylamino)propyl]-11H-pyrido[2,3-b][1,4]benzodiazepin-6(5H)-one, respectively.

EXAMPLE 9 (a to h)

(Illustrates preparation of Formula II Compounds of Chart 1).

Following the procedure of Example 8, the following compounds are reacted with phenyl magnesium chloride:

5-acetyl-11-[3-(dimethylamino)propyl]-11H-pyrido[2,3-b][1,4]benzodiazepin-6(5H)-one, 5-acetyl-11-[3-(dimethylamino)propyl]-11H-pyrido[3,4-b][1,4]benzodiazepin-6(5H)-one, 11-acetyl-5-[3-(dimethylamino)propyl]-5H-pyrido[4,3-b][1,4]benzodiazepin-10(11H)-one, 11-acetyl-5-[3-(dimethylamino)propyl]-5H-pyrido[3,2-b][1,4]benzodiazepin-10(11H)-one, 5-acetyl-11-[3-(tetrahydro-2H-pyran-2-yloxy)propyl]-11H-pyrido[2,3-b][1,4]benzodiazepin-6(5H)-one, 5-acetyl-11-[3-(tetrahydro-2H-pyran-2-yloxy)propyl]-11H-pyrido[3,4-b][1,4]benzodiazepin-6(5H)-one, 11-acetyl-5-[3-(tetrahydro-2H-pyran-2-yloxy)propyl]-5H-pyrido[4,3-b][1,4]benzodiazepin-10(11H)-one, and 11-acetyl-5-[3-(tetrahydro-2H-pyran-2-yloxy)propyl]-5H-pyrido[3,2-b][1,4]benzodiazepin-10(11H)-one, to give mixtures containing the following, respectively:

(a) N-[2-[(2-benzoylphenyl)[3-(dimethylamino)propyl]amino]-3-pyridinyl]acetamide, (b) N-[3-[(2-benzoylphenyl)[3-(dimethylamino)propyl]amino]-4-pyridinyl]acetamide, (c) N-[4-[(2-benzoylphenyl)[3-(dimethylamino)propyl]amino]-3-pyridinyl]acetamide, (d) N-[3-[(2-benzoylphenyl)[3-(dimethylamino)propyl]amino]-2-pyridinyl]acetamide, (e) N-[2-[(2-benzoylphenyl)[3-(tetrahydro-2H-pyran-2-yloxy)propyl]amino]-3-pyridinyl]acetamide, (f) N-[3-[(2-benzoylphenyl)[3-(tetrahydro-2H-pyran-2-yloxy)propyl]amino]-4-pyridinyl]acetamide, (g) N-[4-[(2-benzoylphenyl)[3-(tetrahydro-2H-pyran-2-yloxy)propyl]amino]-3-pyridinyl]acetamide, and (h) N-[3-[(2-benzoylphenyl)[3-(tetrahydro-2H-pyran-2-yloxy)propyl]amino]-2-pyridinyl]acetamide.

EXAMPLE 10

N,N-Dimethyl-6-phenyl-11H-pyrido[2,3-b][1,4]benzodiazepine-11-propanamine fumarate [1:1].

(Illustrates preparation of Formula I compounds, see Chart 1).

The mixture obtained in Example 8 was dissolved in 40 ml of 3N hydrochloric acid and the resulting solution was heated at reflux for 2 hr. During this acid treatment, the N-[2-[(2-benzoylphenyl)[3-(dimethylamino)propyl]amino]3-pyridinyl]isobutyramide was converted to the title compound and the 11-[3-(dimethylamino)propyl]-5-[2-methyl-1-oxopropyl]-11H-pyrido[2,3-b][1,4]benzodiazepin-6(5H)-one was converted to 11-[3-(dimethylamino)propyl]-11H-pyrido[2,3-b][1,4]benzodiazepin-6(5H)-one. The reaction mixture was worked up by an acid-base transfer extraction sequence as described in Preparation 2, followed by evaporation, to give 3.5 g of brown syrup which solidified on standing. Mass spectroscopy at this point showed that a mixture of compounds m/e:297 and 357 was present. Proton NMR indicated the title compound was present in molar ratio of about 1:3 to the 11-[3-(dimethylamino)propyl]-11H-pyrido[2,3-b][1,4]benzodiazepin-6(5H)-one. The brown solid mixture was chromatographed on 95 g of silica gel and eluted first with 5% triethylamine in methylene chloride and then with methanol added to triethylamine in methylene chloride gradient-wise. The free base of the title compound was eluted out first to give, after evaporation, 1.23 g of brown oil. The oil was dissolved in isopropyl alcohol. Fumaric acid, 0.4 g, was added and the mixture was heated. The crystalline title fumarate salt in amount of 1.20 g exhibited essentially identical analysis by m.p. 169°-170° C., TLC, Proton NMR and mass spectroscopy to known title compound prepared, for example, as in U.S. Pat. No. 4,447,361. The yield of title compound based on starting N-[2-[(2-benzoylphenyl)[3-(dimethylamino)propyl]amino]-pyridinyl]isobutyramide was 10% of theoretical. The amount of 11-[3-(dimethylamino)propyl]-11H-pyrido[2,3-b][1,4]benzodiazepin-6(5H)-one recovered from the last effluent from the chromatograph was 2.33 g.

EXAMPLE 11 (a to h)

(Illustrates preparation of Formula I compounds, see Chart 1).

Following the procedure of Example 6, the mixtures a to h prepared in Example 9 are each treated and worked up to give the following compounds:

(a) N,N-dimethyl-6-phenyl-11H-pyrido[2,3-b][1,4]benzodiazepine-11-propanamine fumarate, (b) N,N-dimethyl-6-phenyl-11H-pyrido[3,4-b][1,4]benzodiazepine-11-propanamine fumarate, (c) N,N-dimethyl-10-phenyl-5H-pyrido[4,3-b][1,4]benzodiazepine-5-propanamine fumarate, (d) N,N-dimethyl-10-phenyl-5H-pyrido[3,2-b][1,4]benzodiazepine-5-propanamine fumarate, (e) 6-phenyl-11H-pyrido-11-[3-(tetrahydro-2H-pyran-2-yloxy)propyl]-[2,3-b][1,4]benzodiazepine, (f) 6-phenyl-11H-pyrido-11-[3-(tetrahydro-2H-pyran-2-yloxy)propyl]-[3,4-b][1,4]benzodiazepine, (g) 10-phenyl-5-[3-(tetrahydro-2H-pyran-2-yloxy)propyl]-5H-pyrido[4,3-b][1,4]benzodiazepine, (h) 10-phenyl-5-[3-(tetrahydro-2H-pyran-2-yloxy)propyl]-[3,2-b][1,4]benzodiazepine.

What is claimed is:

1. A process for the preparation of an N-substituted-aryl-pyrido[1,4]benzodiazepine selected from those having the formula:

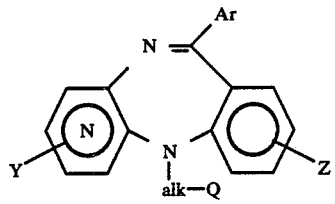

wherein;

Q is —NR$^1$R$^2$ or

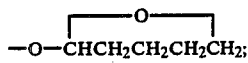

R$^1$ and R$^2$ are selected from loweralkyl or R$^1$ and R$^2$ taken together with the adjacent nitrogen atom may form a heterocyclic residue selected from the group consisting of 1-pyrrolidinyl, 1-piperidinyl, 4-morpholinyl and 4-loweralkyl-piperazin-1-yl;

Ar is selected from phenyl, 2-fluorophenyl, 4-methylphenyl and 4-trifluoromethylphenyl;

Y and Z are selected from hydrogen, loweralkyl or loweralkoxy;

alk is a straight or branched connecting saturated alkylene chain of 1–8 carbons and the acid addition salts thereof, which comprises the steps of Step 1, reacting a compound having the formula:

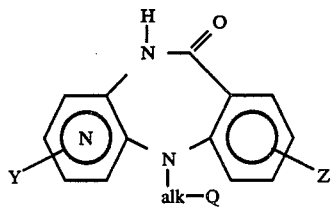

wherein Y, Z, alk and Q have the values given above with an acid anhydride having the formula:

(RCO)$_2$O wherein R is methyl or isopropyl, to give a compound having the formula:

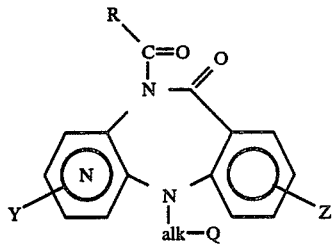

wherein Y, Z, R, alk and Q have the values given above;

Step 2, reacting a compound prepared in Step 1 with a Grignard reagent having the formula:

ArMgX wherein Ar is as defined above and X is Cl, Br or I, to give a mixture containing a compound having the formula:

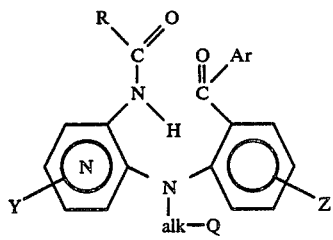

wherein;

Ar, R, Y, Z, alk and Q are the same as for the reactants; and

Step 3, heating the mixture obtained in Step 2 together with a strong acid to give a mixture containing said N-substituted-aryl-pyrido[1,4]benzodiazepine and isolating said benzodiazepine from the mixture.

* * * * *